United States Patent [19]
Pan et al.

[11] Patent Number: 5,731,255
[45] Date of Patent: Mar. 24, 1998

[54] CATALYTIC SYSTEMS AND METHODS FOR CARBONYLATION

[75] Inventors: Li Rui Pan; Tomohide Ina, both of Himeji; Kazuyuki Matsuoka, Kitakatsuragi-gun, all of Japan

[73] Assignee: Daicel Chemical Industries, Ltd., Osaka, Japan

[21] Appl. No.: 504,547

[22] Filed: Jul. 20, 1995

[30] Foreign Application Priority Data

| Jul. 22, 1994 | [JP] | Japan | 6-192022 |
| Mar. 7, 1995 | [JP] | Japan | 7-077353 |
| Mar. 7, 1995 | [JP] | Japan | 7-077354 |

[51] Int. Cl.⁶ .............. C07L 37/36; B01J 31/00
[52] U.S. Cl. .............. 502/155; 502/162; 502/166; 560/207
[58] Field of Search .............. 502/155, 162, 502/160; 560/202

[56] References Cited

U.S. PATENT DOCUMENTS

| 4,325,834 | 4/1982 | Bartish et al. |
| 5,218,111 | 6/1993 | Scholl |
| 5,304,524 | 4/1994 | Klobucar et al. |

FOREIGN PATENT DOCUMENTS

| 1330982 | 7/1994 | Canada |
| 0106379 | 4/1984 | European Pat. Off. |
| 0235864 | 9/1987 | European Pat. Off. |
| 0269395 | 6/1988 | European Pat. Off. |
| 0274795 | 7/1988 | European Pat. Off. |
| 0279447 | 8/1988 | European Pat. Off. |
| 0336215 | 10/1989 | European Pat. Off. |
| 0441446 | 8/1991 | European Pat. Off. |
| 0477516 | 4/1992 | European Pat. Off. |
| 0489472 | 6/1992 | European Pat. Off. |
| 0495548 | 7/1992 | European Pat. Off. |
| 0499329 | 8/1992 | European Pat. Off. |
| 0539628 | 5/1993 | European Pat. Off. |
| 0559288 | 9/1993 | European Pat. Off. |
| 529212 | 7/1986 | Japan |
| 61-176549 | 8/1986 | Japan |
| 6272649 | 4/1987 | Japan |
| 63-154646 | 6/1988 | Japan |
| 4-215851 | 8/1992 | Japan |
| 4-215852 | 8/1992 | Japan |

*Primary Examiner*—Paul J. Killos
*Attorney, Agent, or Firm*—Birch, Stewart, Kolasch & Birch, LLP

[57] ABSTRACT

A carbonylation catalytic system comprises (A) a combination of (A1) a Group VIII metal source of Periodic Table of the Elements (e.g., palladium, palladium chloride) supported on a carrier, (A2) a ligand such as triphenylphosphine and (A3) an acid such as an alkyl-sulfonic acid, or (B) a combination of (B1) the Group VIII metal source except for palladium (e.g., a platinum compound), (B2) a ligand such as triphenylphosphine and (B3) an electron donative compound having an electron donability $\Delta vD$ of not less than 2 (for instance, an amine such as a heterocyclic tertiary amine). The catalytic system (B) may further comprise (B4) an acid such as methanesulfonic acid. In the presence of the catalytic system (A) or (B), an acetylenic or olefinic unsaturated compound is allowed to react with carbon monoxide and a nucleophilic compound having an active hydrogen such as water, an alcohol and a carboxylic acid in a liquid phase to give an unsaturated or saturated carboxylic acid or an ester thereof with high transformation rate and selectivity.

28 Claims, No Drawings

CATALYTIC SYSTEMS AND METHODS FOR CARBONYLATION

FIELD OF THE INVENTION

This invention relates to catalytic systems useful for carbonylation, and to methods for carbonylation of an acetylenic or olefinic unsaturated compound with the use of the catalytic system.

BACKGROUND OF THE INVENTION

Catalytic systems and technologies for carbonylation of an acetylenic or olefinic unsaturated compound have been proposed. Typical carbonylation reactions include a method which comprises allowing an acetylenic or olefinic unsaturated compound to react with carbon monoxide and a nucleophilic compound. In this method, a carbonylation catalyst comprises a Group VIII metal source of Periodic Table of the Elements and a phosphine which is a typical ligand.

EP-A1-106379, EP-A1-235864, EP-A1-274795 and EP-A1-279447 disclose catalytic systems for carbonylation comprising a palladium compound, a triarylphosphine and a proton acid and methods for carbonylation of an acetylenic unsaturated compound and an olefinic compound with the use of such catalytic systems.

Japanese Patent Publication No. 29212/1993 (JP-B-5-29212), Japanese Patent Application Laid-open No. 176549/1986 (JP-A-61-176549), Japanese Patent Application Laid-open No. 72649/1987 (JP-A-62-72649) and Japanese Patent Application Laid-open No. 154646/1988 (JP-A-63-154646) disclose carbonylation catalytic systems comprising a bivalent palladium compound, an organic phosphine and a proton acid, and methods for carbonylation of an acetylenic unsaturated compound and an olefinic compound by using the catalytic systems. The Japanese Patent Application Laid-open No. 154646/1988 (JP-A-63-154646) describes that a homogeneous compound is rather preferred as the palladium compound than a heterogeneous compound and that a phosphine having a heterocyclic group is used as the organic phosphine and, as an inert solvent, N-methylpyrrolidone is preferred.

Further, Japanese Patent Application Laid-open No. 215851/1992 (JP-A-4-215851) discloses a catalytic system for carbonylation which comprises a Group VIII metal source of Periodic Table of the Elements, a phosphine substituted With an aromatic substitute containing an imino-nitrogen atom, a proton source and an anion source of an alkylsulfonic acid, and a method for carbonylation of anacetylenic unsaturated compound and an olefinic compound using the catalytic system. Moreover, Japanese Patent Application Laid-open No. 215852/1992 (JP-A-4-215852) discloses a catalytic system comprising a Group VIII metal source, a phosphine having an imino-nitrogen atom-containing aromatic substituent, a proton source and an anion source of an alkylsulfonic acid, and a method of carbonylation of an acetylenic or olefinic unsaturated compound with the use of the catalytic system. There is described in these literatures, JP-A-4-215851 and JP-A-4-215852, that as the Group VIII metal source of Periodic Table of the Elements, a compound containing the Group VIII metal, specifically a palladium compound is rather preferred than an element in a metallic state.

According to these technologies, a methacrylic acid ester, for example, Can be obtained from methylacetylene, carbon monoxide and an alcohol without using sulfuric acid in a large quantity. Therefore, these technologies are superior to the acetone-cyanohydrin method for a production of a methacrylic acid ester in a point that a methacrylic acid ester can be produced without exhausting industrial wastes such as waste sulfuric acid.

The catalytic systems used in the methods have, however, a significant disadvantage that they have a short catalyst life although having an initial activity to a certain extent, and thus they are not suitable as a catalyst for commercial use. By way of illustration, in carbonylation of an acetylenic unsaturated compound, use of a heterogeneous catalytic system comprising a catalytic component in a metallic state such as palladium black as the catalytic system results in not so much high catalytic activity and causes a significant decrease of the catalytic activity in a short period. When a homogeneous catalytic system containing a palladium compound such as palladium chloride is used as the catalytic system, the palladium compound is reduced in the course of the reaction to precipitate as a metallic simple substance in the reaction system, and a ligand such as an organic phosphine is oxidized which results in a decreased catalytic activity.

In fact, a practical use of a palladium compound as a component of the above-mentioned catalytic system in a carbonylation reaction results in metalation of palladium to rapidly precipitate or dispose in the reaction mixture and thus in decrease of the catalytic activity and reaction rate for carbonylation.

Further, as set forth in the Japanese Patent Application Laid-open No. 215852/1992 (JP-A-4-215852), when a catalytic system comprising a Group VIII element and an triarylphosphine as base components is incorporated with a tertiary amine, the catalytic properties of the catalyst is quite decreased in a carbonylation of an olefin. Therefore, in the method using a tertiary amine such as pyridine as described in the Japanese Patent Application Laid-open No. 215852/1992 (JP-A-4-215852), a phosphine having an aromatic substituent containing an imino-nitrogen atom (e.g., bisphenyl-2-pyridylphosphine) is required to be used as the phosphine, and components for the catalytic system are remarkably restricted. Moreover, the catalytic system comprising a palladium compound as the catalytic component shows insufficient catalytic activity.

SUMMARY OF THE INVENTION

Accordingly, it is an object of the present invention to provide a carbonylation catalytic system whereby, even though being a heterogeneous catalytic system, a high catalytic activity can be obtained and maintained for a long period, and a method for carbonylation using the catalytic system.

Another object of the present invention is to provide a catalytic system whereby, even if containing a palladium source, a decrease of the catalytic activity can be suppressed and thus carbonylation can be conducted with high transformation rate and selectivity and with high stability, and a method for carbonylation with the use of such catalytic system.

It is a further object of the invention to provide a catalytic system and a method for carbonylation whereby a carbonylation product such as a carboxylic acid and a carboxylic acid ester can be produced by carbonylation of an acetylenic or olefinic unsaturated compound in a stable liquid phase system with maintaining high transformation rate and selectivity for a long duration.

A yet further object of the present invention is to provide a catalytic system and a method for carbonylation which are useful for producing an α,β-ethylenic unsaturated carboxylic acid or a derivative thereof such as methyl methacrylate with high transformation rate and selectivity and with maintaining high stability for a long period.

It is another object of the present invention to provide a catalytic system for carbonylation having, regardless of comprising a tertiary amine or not, high stability and high catalytic activity without the use of a special phosphine having an imino-nitrogen atom-containing aromatic substituent, and a method for carbonylation utilizing such catalytic system.

It is a further object of the invention to provide a stabilized catalytic system whereby carbonylation can be carried out with high transformation rate and selectivity, and a method for carbonylation using the catalytic system.

A yet another object of the present invention is to provide a catalytic system and a method for carbonylation whereby a carbonylation product such as a carboxylic acid and a carboxylic acid ester can be produced by carbonylation of an acetylenic or olefinic unsaturated compound in a stable liquid phase system with maintaining high transformation rate and selectivity.

A still further object of the present invention is to provide a catalytic system and a method for carbonylation which are useful for producing an α,β-ethylenic unsaturated carboxylic acid or a derivative thereof such as methyl methacrylate with high transformation rate and selectivity.

After intensive investigation and research to accomplish the above objects, the inventors of the present invention found that when a Group VIII metal of Periodic Table of the Elements such as palladium is supported on a carrier and is used in a catalytic system in combination with a ligand such as an organic phosphine and an acid such as an alkylsulfonic acid, a high catalytic activity can be obtained in spite of being a heterogeneous catalytic system, and moreover, decrease of such catalytic activity can significantly be suppressed or restrained.

They further found that a combination use of a Group VIII element of Periodic Table of the Elements except for palladium, a non-heterocyclic ligand which does not contain a nitrogen atom as a hetero atom, and a specific electron donative compound can suppress or prevent decrease of the catalytic activity, and remarkably improve or enhance the catalytic activity in combination with an amine, and that when using platinum, typically speaking, the catalytic activity can further be enhanced and a carbonylation product can be produced with high selectivity.

The present invention has been accomplished based on the above findings.

Thus, the carbonylation catalytic system (A) of the present invention comprises a combination of (A1) a Group VIII metal source of Periodic Table of the Elements, (A2) a ligand and (A3) an acid.

The Group VIII metal source of Periodic Table of the Elements (A1) may be cobalt, nickel, rhodium, palladium or platinum, or a compound of such metal. The carrier may be an activated carbon, an oxide of a metal or nonmetal oxide or a clay mineral. The specific surface area of the carrier may be about 10 to 3,000 m²/g. The supporting amount of the Group VIII metal source (A1) may frequently be about 0.01 to 20% by weight relative to the carrier. The ligand (A2) may be a phosphorus compound such as a tertiary organic phosphine and others; an arsenic compound such as a tertiary organic arsine and the like; or an antimony compound. As the acid, use may be made of a proton acid (a Brönsted acid) such as an arylsulfonic acid, an alkylsulfonic acid, a carboxylic acid, a hydrohalogenic acid, sulfuric acid, nitric acid, a phosphoric acid, a perhalogenic acid and so on.

The catalytic system for carbonylation (B) according to the present invention comprises a combination of (B1) a Group VIII metal source of Periodic Table of the Elements except for palladium, (B2) a ligand shown by the following formula (Ib), and (B3) an electron donative compound having an electron donability ΔvD relative to deuterated methanol D of not less than 2:

wherein A represents a phosphorus atom, an arsenic atom or an antimony atom; and $R^1$, $R^2$ and $R^3$ independently represent a hydrogen atom, an optionally substituted alkyl group, an optionally substituted alkenyl group, an optionally substituted alkynyl group, an optionally substituted cycloalkyl group or an optionally substituted aryl group, or $R^2$ and $R^3$ may together form an optionally substituted alkylene group, with a proviso that $R^1$ to $R^3$ are not concurrently hydrogen atoms.

The Group VIII metal source (B1) may be the other metal source than palladium such as platinum, cobalt, nickel, rhodium and so on. The ligand (B2) may be a phosphorus compound of the formula (Ib) where A is a phosphorus atom such as an organic phosphine including a tertiary organic phosphine, for instance. The ligand (B2) is characterized by being a compound which does not contain a heterocyclic group having a nitrogen atom as a hetero atom.

The electron donative compound (B3) may be whichever of a compound having an electron donability ΔvD of not less than 2, and may for example be an amine such as a heterocyclic tertiary amine, an alkanolamine, an ether, an ester and others. The catalytic system for carbonylation (B) may further comprise (B4) an acid (proton acid or Lewis acid).

According to the method of the present invention, an acetylenic or olefinic unsaturated compound is allowed to react with carbon monoxide in the presence of the catalytic system (A) or (B) to produce a carbonylation product. Further, the reaction may also be conducted in the presence of a nucleophilic compound having a hydrogen atom which can be left or eliminated (for example, a compound having a hydroxyl group such as water, an alcohol, a carboxylic acid and the like) to give an unsaturated carboxylic acid, a saturated carboxylic acid or a derivative thereof such as an ester or anhydride of the carboxylic acid corresponding to the acetylenic or olefinic unsaturated compound.

DETAILED DESCRIPTION OF THE INVENTION

In this specification, the term "olefinic unsaturated compound" means and includes a compound having an ethylenic unsaturated double bond regardless of the number of such double bond.

The catalytic system (A) of the present invention is now described in detail.

The catalytic system (A) of the present invention comprises (A1) a Group VIII metal source of Periodic Table of the Elements (hereinafter may briefly referred to as Group VIII metal source) which is supported on a carrier or support. The Group VIII metal element includes, for example, iron, ruthenium, osmium, cobalt, rhodium, iridium, nickel, palladium and platinum. On or after the year of 1990, these elements are classified into the Group 8 elements (Fe, Ru, Os), the Group 9 elements (Co, Rh, It) and the group 10 elements (Ni, Pd, Pt) of Periodic Table of the Elements. As preferred elements, there may be mentioned cobalt, nickel, rhodium, palladium and platinum, and specifically preferred are cobalt and palladium. Among them, palladium can advantageously be employed. The oxidation number of such element can be selected according to the species thereof and is not critically restricted. The oxidation number may frequently be 0, +2 or +3, for instance.

The Group VIII metal source may whichever of a simple substance of the metal, or a compound containing the Group VIII element. The catalytic system (A) of the present invention is characterized in that high catalytic activity can be obtained and maintained for a long time, even though using such simple substance of the metal.

Examples of the compound of the Group VIII element include an inorganic acid salt (for instance, a nitrate, a sulfate, a perhalogenate, a hydrohalogenic acid such as hydrochloric acid and hydrobromic acid), an organic acid salt (for example, a sulfonate such as methanesulfonic acid, ethanesulfonic acid, benzenesulfonic acid and p-toluenesulfonic acid, a phosphonic acid salt, a salt of a carboxylic acid having about 20 or less carbon atoms (for example about 12 or less carbon atoms) such as formic acid, acetic acid, propionic acid and others), a halide (a chloride, a bromide and the like), a complex (or a complex salt) and so on. According to the present invention, even when the Group VIII metal source is a hydrohalogenic acid salt of the Group VIII metal such as palladium chloride, a risk of corrosion can be minimized and still more, high catalytic activity can be sustained for a long period of time.

As a ligand constructing the complex, there may be mentioned for example OH (hydroxo), an alkoxy group such as methoxy, ethoxy, propoxy and butoxy groups, an acyl group such as acetyl and propionyl groups, an alkoxycarbonyl group such as methoxycarbonyl (acetato) and ethoxycarbonyl group, acetylacetonato, cyclopentadienyl group, benzylidene group, benzylideneacetone, benzylideneacetylacetone, benzylideneacetophenone, a cycloalkadiene such as cyclooctadiene, a halogen atom such as chlorine atom and bromine atom, CO, CN, oxygen atom, $H_2O$ (aquo), a phosphine (for instance, a triaryl-phosphine such as triphenylphosphine), a nitrogen-containing compound such as $NH_3$ (ammine), NO, $NO_2$ (nitro), $NO_3$ (nitrato), ethylenediamine, diethylene-triamine, pyridine and phenanthroline. In such complex or complex salt, one or more of ligands of the same or different species may be coordinated.

Examples of the complex include a palladium complex such as acetylacetonepalladium, tetrakis (triphenylphosphine) palladium, bis(tri-o-tolylphosphine) palladium acetate, bis(diphenyl-2-pyridylphosphine) palladium acetate, tetrakis(diphenyl-2-pyridylphosphine) palladium, bis(di-o-toylpyridylphosphine)palladium acetate, bis(diphenylpyridylphosphine)palladium sulfate and others, and corresponding complexes of the above-mentioned Group VIII metals.

As the carrier (support), a conventional carrier whereby dispersing property of the catalytic active component can be improved or enhanced and effective surface area can be increased may be used. Examples of such carrier include an activated carbon; a metal or nonmetal oxide (including a compound oxide) such as silica, alumina, silica-alumina, magnesia, silica-magnesia and titania; a clay mineral such as diatomaceous earth, kaolin, bentonite, pumice, asbestos, alundum and corundum; silicon carbide and so on.

As examples of the activated carbon, there may be mentioned, regardless of its origin, an activated carbon obtainable from whichever of a raw material including a carbonizable vegetable (plant) raw material such as wood, charcoal, coconut shell and carbonized products of these materials; a carbonizable mineral raw material such as lignite, coal, coal tar and petroleum pitch; a carbonizable polymer raw material such as phenol resin, furan resin, epoxy resin, acrylic resin and polyacrylonitrile, vinylidene chloride resin. The activated carbon may be a product obtainable by any activating process or treatment such as chemical activation, steam (aqueous vapor) activation and the like.

Preferred examples of the carrier include an activated carbon; a metal or nonmetal oxide such as silica, alumina (including γ-alumina), silica-alumina and titania, and in particular, an activated carbon.

Form (shape) of the carrier may be selected according to the reaction type such as suspension type and fixed-bed type, and is for instance powdery, granular, fibrous structure, pellet structure, honeycomb structure or so forth.

The specific surface area of the carrier may be selected from a range as far as the catalytic activity is not adversely affected, and is, for example, about 0.1 to 3,000 $m^2/g$, usually about 10 to 3,000 $m^2/g$, preferably about 10 to 2,500 $m^2/g$, and more preferably about 50 to 2,000 $m^2/g$ (for instance about 50 to 1,500 $m^2/g$). The carrier having a specific surface area of about 100 to 2,000 $m^2/g$ may frequently be used. When the specific surface area of the carrier is too small, high catalytic activity can hardly be obtained.

The pore volume and mean pore size (diameter) can be any volume and size within a range wherein the activity and stability of the catalyst are not sacrificed. As such, the mean pore size of the carrier may, for example in case of the activated carbon, usually about 5 to 200 Å, and preferably about 10 to 150 Å. The pore volume of the carrier is for example about 0.05 to 7 ml/g, preferably about 0.05 to 3 ml/g, and more preferably about 0.1 to 2 ml/g. Exceedingly small mean pore size or pore volume of the carrier tends to decrease the catalytic activity. Conversely, the catalyst life has a tendency to be shortened because of an excess amount of the mean pore size or pore volume.

Supporting amount of the Group VIII metal source may be chosen within a range insofar as the catalytic activity and the stability of the catalyst, and is, for instance, about 0.01 to 40% by weight, usually about 0.01 to 20% by weight, preferably about 0.1 to 15% by weight, more preferably about 0.2 to 10% by weight and frequently about 0.5 to 5% by weight relative to the amount of the carrier. When too much small amount of the catalyst is supported on the carrier, sufficiently high catalytic activity may hardly be obtained. On the contrary, too much large amount of the supported catalyst may occasionally result in sacrificing the activity and stability of the catalyst as well as economical performance.

Supporting of the Group VIII metal source (A1) on the carrier can be conducted according to a conventional supporting process such as impregnation, coating, spraying, adsorption or precipitation process. By oxidizing or reducing the metal source supported on the carrier, the oxidation number of the metal element can be converted to a desired value. By way of illustration, by supporting a compound of the Group VIII metal having an oxidation number of +2 such as palladium chloride on the carrier and subjecting the supported compound to a treatment with a reducing agent such as formalin, a simple substrate of the Group VIII metal having a oxidation number of 0 such as palladium metal supported on the carrier can be obtained.

The catalytic system (A) of the present invention contains a ligand (A2). This ligand (A2) may frequently be different from the ligand which constitute the metallic compound (complex) of the Group VIII metal as mentioned above. Usually, the ligand (A2) comprises at least one phosphorus atom, arsenic atom, nitrogen atom or antimony atom, and can be coordinated to the Group VIII element. These ligand can be used singly or in combination.

Examples of the ligand (A2) include a ligand shown by the following formula (Ia):

(Ia)

wherein A represents a phosphorus atom, an arsenic atom or an antimony atom; and $R^1$, $R^2$ and $R^3$ independently represent a hydrogen atom, an optionally substituted alkyl group, an optionally substituted alkenyl group, an optionally substituted alkynyl group, an optionally substituted cycloalkyl group, an optionally substituted aryl group or an optionally substituted heterocyclic group, or $R^2$ and $R^3$ may together form an optionally substituted alkylene group, with a proviso that $R^1$ to $R^3$ are not concurrently hydrogen atoms.

In the formula (Ia), the alkyl group includes, for example, a straight-chain or branched-chain alkyl group having about 1 to 10 carbon atoms such as methyl, ethyl, propyl, isopropyl, butyl, isobutyl, sec-butyl, t-butyl, pentyl, hexyl, heptyl, octyl, nonyl and decyl groups. Preferred alkyl group includes, for instance, a lower alkyl group having about 1 to 6 carbon atoms, specifically about 1 to 4 carbon atoms.

As examples of the alkenyl group, there may be mentioned a straight-chain or branched-chain alkenyl group having about 2 to 10 carbon atoms such as vinyl, allyl, isopropenyl, 2-methyl-1-propenyl, 1-butenyl, 2-butenyl, 1-pentenyl, 1-hexenyl, 1-heptenyl, 1-octenyl, 1-nonenyl and 1-decenyl groups. Preferred examples of the alkenyl group include an alkenyl group having about 2 to 6 carbon atoms, and in particular about 2 to 4 carbon atoms. The alkynyl group includes, for example, an alkynyl group having about 2 to 10 carbon atoms such as ethynyl, propynyl, 1-butynyl, 2-butynyl, 1-pentynyl, 1-hexynyl, 1-heptynyl, 1-octynyl, 1-nonynyl and 1-decynyl groups.

Example of the cycloalkyl group includes a cycloalkyl group having about 4 to 10 carbon atoms such as cyclobutyl, cyclopentyl, cyclohexyl and cyclooctyl groups. The aryl group includes, for instance, phenyl group and naphthyl group.

The heterocyclic group includes a heterocyclic group containing a nitrogen atom as a hetero atom, specifically an aromatic heterocyclic group. As such heterocyclic group, there may be mentioned, for example, a pyridyl group such as 2-pyridyl group, a pyrazinyl group such as 2-pyrazinyl group, a quinolyl group such as 2-quinolyl group, an isoquinolyl group such as 1-isoquinolyl group, a-pyrimidinyl group such as 2-pyrimidinyl group, a pyridazinyl group such as 3-pyridazinyl group, cinnolinyl group, triazinyl group, quinoxalinyl group, quinazolinyl group and so on. Preferred example of the heterocyclic group includes pyridyl group, pyrimidinyl group and so forth.

These alkyl group, cycloalkyl group, aryl group and heterocyclic group may have a various substitute which does not affects on the catalytic activity adversely such as a halogen atom, an alkyl group, a hydroxyl group, an alkoxy group, a carboxyl group, an alkoxycarbonyl group, an acyl group, a nitro group or a cyano group.

The halogen atom includes fluorine, chlorine, bromine and iodine atoms. As the alkyl group, there may be mentioned for instance an alkyl group having about 1 to 10 carbon atoms such as methyl, ethyl, propyl, isopropyl, butyl, isobutyl, t-butyl, pentyl, hexyl and other groups, preferably an alkyl group having about 1 to 6 carbon atoms and typically about 1 to 4 carbon atoms.

Example of the alkoxy group includes an alkoxy group having about 1 to 10 carbon atoms, preferably about 1 to 6 carbon atoms such as methoxy, ethoxy, propoxy, isopropoxy, butoxy, isobutoxy, t-butoxy, pentyloxy and hexyloxy groups. Typically preferred alkoxy group includes a lower alkoxy group having about 1 to 4 carbon atoms.

As the alkoxycarbonyl group, there may be mentioned for instance an alkoxycarbonyl group having, in the alkoxy moiety, about 1 to 10 carbon atoms such as methoxycarbonyl, ethoxycarbonyl, propoxycarbonyl, isopropoxycarbonyl, butoxycarbonyl, isobutoxycarbonyl, t-butoxycarbonyl, pentyloxycarbonyl and hexyloxycarbonyl groups. Preferred example of the alkoxycarbonyl group includes a lower alkoxycarbonyl group having, in the alkoxy moiety, about 1 to 6 carbon atoms, and typically about 1 to 4 carbon atoms.

The acyl group includes, for example, an acyl group having about 1 to 6 carbon atoms such as formyl, acetyl, propionyl, butyryl, isobutyryl, valeryl, iso-valeryl and pivaloyl groups.

$R^2$ and $R^3$ may together form an alkylene group having about 1 to 10 carbon atoms such as methylene, ethylene, propylene, isopropylene, isopropylidene and tetramethylene groups, to form a cyclic group containing A. By way of illustration, $R^2$ and $R^3$ may together form a phosphacycloalkylene group having about 3 to 10 carbon atoms together with a phosphorus atom.

Preferred example of the ligand includes an organic phosphorus compound, an organic arsenic compound and an organic antimony compound, typically an organic phosphine and an organic arsine, and specifically an organic phosphine. The organic phosphine may be whichever of a primary phosphine (for example, methylphosphine, ethylphosphine, propylphosphine, isopropylphosphine, isobutylphosphine, isoamylphosphine, phenylphosphine, cyclohexylphosphine and so on), a secondary phosphine (for instance, dimethylphosphine, diethylphosphine, diisopropylphosphine, di-n-butylphosphine, diisoamylphosphine, diphenylphosphine, dicyclohexylphosphine and the like) or a tertiary phosphine. The organic arsine may also be whichever of a primary arsine, a secondary arsine or a tertiary arsine. Preferred example of such organic phosphine and organic arsine includes a tertiary phosphine and a tertiary arsine shown by the formula (Ia).

Preferable organic phosphine may be an organic phosphine of the formula (Ia) wherein at least one of $R^1$ to $R^3$ is an aryl group such as phenyl group or a substituted phenyl group. The heterocyclic group and the alkylene group formed by a combination of $R^2$ and $R^3$ are also preferred as an alternative for the aryl group or as in combination with the aryl group.

As practical examples of the organic phosphine, there may be mentioned (i) an optionally substituted triarylphosphine such as triphenylphosphine, tri(4-methylphenyl) phosphine, tri(3,5-dimethylphenyl)phosphine, tri(2,4,6-trimethylphenyl)phosphine, tri(4-methoxyphenyl) phosphine, tri(3,5-dimethoxyphenyl)phosphine, tri(4-chlorophenyl)phosphine and tri(3,5-dichlorophenyl) phosphine; (ii) a mono-$C_{1-10}$ alkyl-diarylphosphine such as methyldiphenylphosphine, ethyldiphenylphosphine, propyldiphenylphosphine and butyldiphenylphosphine; (iii) a di-$C_{1-10}$ alkyl-monoarylphosphine such as dimethylphenylphosphine, diethylphenylphosphine, dipropylphenylphosphine and dibutylphenylphosphine; (iv) a tri-$C_{1-10}$ alkyl-phosphine such as trimethylphosphine, triethylphosphine, tributylphosphine, triamylphosphine, trihexylphosphine and the like; (v) a mono-$C_{4-10}$ cycloalkyldiarylphosphine such as cyclopentyldiphenylphosphine and cyclohexyldiphenylphosphine; (vi) a di-$C_{4-10}$ cycloalkyl-monoarylphosphine such as dicyclopentylphenylphosphine and dicyclohexylphenylphosphine; (vii) a tri-$C_{4-10}$ cycloalkylphosphine such as tricyclopentylphosphine and tricyclohexylphosphine; (viii) a phosphine having a heterocyclic group such as 2-pyridylbisphenylphosphine, bis(2-pyridyl)phenylphosphine, tris(2-pyridyl)phosphine, 2-pyridylbismethylphosphine, bis(2-pyridyl) methylphosphine, 2-pyridylbisethylphosphine, bis(2-pyridyl)ethylphosphine, 2-pyridylbisbutylphosphine, bis(2-pyridyl)butylphosphine, 6-methyl-2-pyridylbisphenylphosphine, bis(6-methyl-2-pyridyl)-phenylphosphine, tris(6-methyl-2-pyridyl)phosphine, 6-ethyl-2-pyridylbisphenylphosphine, bis(6-ethyl-2-pyridyl)-phenylphosphine, tris(6-ethyl-2-pyridyl) phosphine, 6-butyl-2-pyridylbisphenylphosphine, bis(6-butyl-2-pyridyl)-phenylphosphine, tris(6-butyl-2-pyridyl) phosphine, 4,6-dimethyl-2-pyridylbisphenyl-phosphine, 6-methoxy-2-pyridylbisphenylphosphine, bis(6-methoxy-2-pyridyl) phenylphosphine, tris(6-methoxy-2-pyridyl)-phosphine, 6-chloro-2-pyridylbisphenylphosphine, bis(6-chloro-2-pyridyl)phenylphosphine, tris(6-chloro-2-pyridyl) phosphine, 4,6-dichloro-2-pyridylbisphenylphosphine, 6-bromo-2-pyridylbisphenylphosphine, bis(6-bromo-2-pyridyl)phenylphosphine, 2,6-bis(diphenylphosphino) pyridine, 2,6-bis(di-p-tolylphosphino)-pyridine and so on; (ix) other phosphine such as ethane-1,2-diylbisdiphenylphosphine, ethane-1,2-diylbis [bis (trifluoromethyl)phosphine], ethene-1,2-diylbisdiphenylphosphine, ethyne-1,2-diylbisdiphenylphosphine, 1,2-phenylenebisdiphenylphosphine, hexafluorocyclopentene-1,2-diylbisdiphenylphosphine, tetrafluorocyclobutene-1,2-diylbisdiphenylphosphine, octafluorocyclohexene-1,2-diylbisdiphenylphosphine, 1,4-diphenyl-1,4-diphosphacyclohexane, bis(1,2-diphenyl)phosphenomethyl-cyclobutane and so forth.

As preferred organic arsine, there may be mentioned an organic arsine corresponding to the preferred organic phosphine as mentioned above, including an optionally substituted triarylarsine such as triphenylarsine; a mono-$C_{1-10}$ alkyl-diarylarsine such as ethyldiphenylarsine; a di-$C_{1-10}$ alkyl-monoarylarsine such as diethylphenylarsine and others. An antimony compound (typically, a tertiary organic stibine) corresponding to the above-exemplified phosphorus compound may also preferably be employed as the ligand.

The ligand (A2) may be supported on the carrier together with the Group VIII metal source. Supporting of such ligand can be conducted according to a conventional technology, for example, the process as mentioned above.

As the acid (A3) constituting the catalytic system (A), a variety of proton acids (inorganic acids and organic acids) and Lewis acids can be used. The proton acid includes, for example, sulfuric acid, a hydrohalogenic acid, nitric acid, phosphoric acid, a sulfonic acid (for instance, an arylsulfonic acid, an alkylsulfonic acid and the like), phosphonic acid, a carboxylic acid, perhalogenic acid and a heteropolyacid. These acid may be used singly or in combination. The acid may probably act or function as a proton source (proton donor). Therefore, when employing a Lewis acid, such Lewis acid may frequently be used in combination with other proton source.

As the inorganic compound among the proton acids, there may be exemplified with sulfuric acid; a hydrohalogenic acid such as hydrochloric acid and hydrobromic acid; a phosphoric acid (for example, orthophosphoric acid or pyrophosphoric acid); perhalogenic acid such as perchloric acid; a heteropolyacid containing V, W or Mo such as phosphomolybdic acid, tungstosilicic acid and vanadomolybdic acid.

Among such proton acids, the organic compound includes, for instance, an optionally substituted arylsulfonic acid such as benzenesulfonic acid, p-toluenesulfonic acid and naphthalenesulfonic acid; an optionally substituted alkylsulfonic acid such as methanesulfonic acid, ethanesulfonic acid, propanesulfonic acid, t-butylsulfonic acid, 2-hydroxypropanesulfonic acid, trifluoromethanesulfonic acid and trichloromethanesulfonic acid; a phosphonic acid such as benzenephosphonic acid; a carboxylic acid including an optionally substituted saturated aliphatic carboxylic acid such as chloroacetic acid, dichloroacetic acid, trichloroacetic acid, trifluoroacetic acid, formic acid, acetic acid, propionic acid, n-butyric acid, isobutyric acid, pivalic acid, valeric acid, caproic acid, caprylic acid, capric acid, lauric acid, myristic acid, palmitic acid, stearic acid and oxalic acid, an alicyclic acid such as cyclohexanecarboxylic acid, an aromatic carboxylic acid such as benzoic acid, phthalic acid, isophthalic acid and terephthalic acid, an unsaturated aliphatic carboxylic acid such as acrylic acid, methacrylic acid, propionic acid, crotonic acid, maleic acid, fumaric acid, citraconic acid, mesaconic acid and oleic acid; an amino acid such as aspartic acid, glutamic acid and so forth. The acid may be an acidic ion exchange resin such as an ion exchange resin having a sulfonic acid group, a phosphonic acid group or a phosphinic acid group, for example.

Example of the Lewis acid includes a halide of an element belonging to the Group VIIIB, the Group IVA, the Group IVB, th Group VA or the Group VB of Periodic Table of the Elements, or a complex compound thereof such as $BF_3$, $BF_3 \cdot O(C^2H_5)_2$, $AlCl_3$, $TiCl_4$, $Ti[OCH(CH_3)_2]_4$, $SnCl_4$, $SnCl_2$, $NbF_5$, $TaF_5$, $PF_5$, $AsF_5$ and $SbF_5$; or an alkoxide (for example, a $C_{1-5}$ alkoxide).

The acid may usually have an anion capable of coordinating. As preferred example of the acid, there ay be mentioned a proton acid (Brönsted acid) including an arylsulfonic acid such as p-toluenesulfonic acid; an alkylsulfonic acid having about 1 to 10 carbon atoms, preferably about 1 to 6 carbon atoms, and more preferably an alkylsulfonic acid having about 1 to 4 carbon atoms such as methanesulfonic acid; an aliphatic carboxylic acid, preferably an aliphatic unsaturated carboxylic acid having about 2 to 10 carbon atoms; an inorganic acid (for instance, sulfuric acid, a hydrohalogenic acid or a phosphoric acid).

The acid may be supported on the carrier with the Group VIII metal source. Such acid can be supported according to a conventional method such as a technology as mentioned above.

The catalytic system (A) of the present invention may further comprises an electron donative (electron repelling) compound. As the electron donative compound, a compound having an electron donability $\Delta vD$ of not less than 2 may be used, for example. The electron donability means a sift value of wave number of O-D non-conjunctive stretching vibration of a deuterated (deuterium-containing) methanol (0.4 mol per liter) in a liquid compound when benzene is used as a primary standard, and is defined as "an electron donability $\Delta vD$ relative to methanol D". Such electron donative compound may probably have coordinating properties to the Group VIII element.

As such electron donative compound, there may be exemplified with an amine, an imine, an amide, a sulfoxide, an aldehyde, an ether, a ketone, a lactone, an ester, a nitrile, a nitro compound, an aromatic hydrocarbon, an aliphatic hydrocarbon and so on. These compounds may be used singly or in combination.

With respect to the electron donability ΔvD, there can be referred to, for instance, "Solvent Effect on Organic Chemical Reaction" written by Senoo and Arai, published by Sangyo Tosho Co., Ltd., Japan on Apr. 25, 1976. For the following electron donative compounds as examples, the value of the electron donability ΔvD is indicated in a parenthesis, for reference.

The amine includes, for instance, an aliphatic amine such as methylamine, ethylamine (233), n-propylamine (230), n-butylamine, diethylamine, di-n-propylamine (242), dibutylamine and triethylamine (238); an alicyclic amine such as cyclohexylamine; an aromatic amine such as aniline (158), N-methylaniline (151) and N,N-dimethylaniline (148); an alkanolamine such as dimethanolamine, trimethanolamine, ethanolamine, diethanolamine, triethanolamine, dipropanolamine, tripropanolamine, butanolamine, dibutanolamine, tributanolamine, dimethylaminoethanol and diethylaminoethanol; a heterocyclic amine such as morpholine, N-methylpyrrolidone, pyrrole, imidazole, 1-methylimidazole, pyridine (168), α-picoline (183), β-picoline, γ-picoline (160), 2,3-lutidine, 2,4-lutidine, 2,5-lutidine, 2,6-lutidine, 3,4-lutidine, 3,5-lutidine, 2-ethylpyridine, 3-ethylpyridine, 4-ethylpyridine (179), 2,3,4-trimethylpyridine, 2,4,6-trimethylpyridine, dipyridine, o-toluidine (145), piperidine (240), 4-vinylpyridine (193), pyrazine, pyrimidine, quinoline, isoquinoline and the like. The amine also includes a resin and an ion exchange resin having a basic group such as amino group, a substituted amino group including, for instance, a monoalkylamino group or a dialkylamino group and quaternary ammonium group (e.g. an amine resin such as a pyridine resin obtainable from a reaction of pyridine and formaldehyde).

Typical example of the amine includes a secondary amine and a tertiary amine, and specifically a heterocyclic amine containing a nitrogen atom as a hetero atom (for example, pyridine, imidazole, etc.) or a derivative thereof and an alkanolamine. The derivative of such heterocyclic amine includes, for instance, a compound substituted with an alkyl group having about 1 to 4 carbon atoms and others (e.g. picoline, lutidine, dipyridine, 1-methylimidazole and so on). The heterocyclic amine such as pyridine and its derivative may frequently have aromaticity.

Example of the imine includes ethyleneimine (237), N-phenylethyleneimine (186) and so forth. The amide includes, for instance, formamide, acetamide, N,N-dimethylformamide (107), N,N-dimethylacetamide (113), tetramethylurea and hexamethylphosphamide. As the sulfoxide, there may be mentioned dimethylsulfoxide (141), diisopropylsulfoxide, sulfolane, 2-methylsulfolane and 3-methylsulfolane, for instance.

The aldehyde includes, for example, an aliphatic aldehyde such as acetaldehyde (79), propionaldehyde (85), n-butylaldehyde (83), acrolein (122), metacrolein and crotonaldehyde (75); and an aromatic aldehyde such as benzaldehyde (53).

Example of the ether includes a chain ether such as diethyl ether (78), di-n-propyl ether (73), di-isopropyl ether (75), ethyl n-butyl ether (77), ethyl vinyl ether (31), n-butyl vinyl ether (33), isobutyl vinyl ether (33), diallyl ether (66), 1,2-dimethoxyethane (71), cellosolve (ethylene glycol monoethyl ether), carbitol (diethylene glycol ethyl ether), diglyme [bis(2-methoxyethyl) ether], diethylene glycol dimethyl ether and diethylene glycol diethyl ether; an aromatic ether such as anisole (26), phenetole (25), 1,2-dimethoxybenzene and diphenyl ether; and a cyclic ether such as propylene oxide (59), styrene oxide (51), 3,3-bischloromethyloxetane (78), furan (4), tetrahydrofuran (90), 1,3-dioxolane (58), 2-methyl-1,3-dioxolan (61), 4-methyl-1,3-dioxolan (56), 2-phenyl-1,3-dioxolan (56), 4-chloromethyl-1,3-dioxolan (43), tetrahydropyran (93) and 1,4-dioxane (77).

Typical use is made of an aromatic ether having an optionally substituted aryl group (for instance, anisole) or a chain ether (e.g. diethylene glycol dimethyl ether) among these ethers.

As the ketone, there may be mentioned for example an aliphatic ketone such as acetone (64), methyl ethyl ketone (57), diethyl ketone (56), diisopropyl ketone, methyl vinyl ketone (89) and methyl isobutyl ketone; an alicyclic ketone such as cyclohexanone(66); an aromatic ketone such as acetophenone (56) and so forth. Example of the lactone includes β-propiolactone (34), γ-butyrolactone (66), ε-caprolactone (82) and so on.

The ester includes, for instance, an organic carboxylic acid alkyl ester such as methyl acetate (36), ethyl acetate (39), methyl chloroacetate (27), butyl acetate, methyl dichloroacetate (23), methyl propionate (33), ethyl propionate (32) and methyl isobutyrate (32); a vinyl ester such as vinyl acetate (21); an unsaturated carboxylic acid alkyl ester such as methyl acrylate (30), ethyl acrylate (33), methyl methacrylate (37), methyl crotonate and ethyl crotonate. Even when an unsaturated carboxylic acid alkyl ester (e.g. methyl methacrylate, methyl crotonate, etc.) is used as the ester, the reaction may proceed smoothly.

As example of the nitrile, there may be mentioned acetonitrile (49), propionitrile (52), butyronitrile, acrylonitrile (37), benzonitrile (38) and others. Example of the nitro compound includes an aliphatic nitro compound such as nitromethane (6) and nitroethane (8), an aromatic nitro compound such as nitrobenzene (21). The aromatic hydrocarbon includes, for example, toluene (2), xylene (4), ethylbenzene (4), styrene (2), α-methylstyrene (4) and p-methylstyrene (2). Example of the aliphatic hydrocarbon includes ethylene chloride (2).

Practically, an electron donative compound having an electron donability ΔvD of about 4 to 250, preferably about 10 to 230 (for instance, about 20 to 200) may be used among these compounds. A compound having an electron donability ΔvD of about 30 to 250, preferably about 50 to 250 (e.g. about 100 to 250) may also be included in such preferred electron donative compounds. The electron donative compound may frequently be used as a reaction solvent in order to simplify the preparing process of the catalytic system.

From the standpoint of operating properties of the reaction or others, a compound which is other than a vinyl compound (that is, a non-polymerizable compound) and does not adversely affects on the carbonylation is typically employed. As such compound, there may be mentioned, for instance, the amine such as a tertiary amine, the amide, the sulfoxide, the ether, the ketone, the ester, the nitrile, the nitro compound and the aromatic hydrocarbon (specifically, the amine, the ether, the ester and the aromatic hydrocarbon).

Preferred example of the electron donative compound includes a basic compound such as the amine, the imide and the amide. Typically, when use is made of such basic compound (especially, a secondary amine and a tertiary amine) in combination with the Group VIII metal source (typically, a palladium source), the catalytic activity can significantly be improved or enhanced in many cases. Therefore, the catalytic system (A) may preferably comprise a basic compound selected from the group consisting of the amine, the imide and the amide. Further, combination use of these basic compounds with the ether and/or the ester may occasionally increase or enhance the transformation rate and the selectivity of the reaction.

In the catalytic system (A) of the present invention, the ligand and the electron donative compound can be used in a suitable combination according to species of the metal source. By way of illustration, a combination use of the Group VIII metal source (A1) (for example, a palladium source) and an organic phosphine as the ligand may not sacrifice the stability or activity of the catalyst, regardless of species of the organic phosphine. Therefore, the organic phosphine can be used in a suitable combination with the compound having an electron donability ΔvD of not less than 2. When a triarylphosphine is employed as the organic phosphine, for example, the nitrogen-containing compound pound or the basic compound, including an amine compound pound such as pyridine or its derivative as mentioned above, is frequently employed for significant increase or improvement of not only the stability but also the activity of the catalyst.

Proportions of each components of the catalytic system may be selected from a range according to species of each of the catalytic components, where the catalytic activity due to an interaction or correlation of the Group VIII metal source supported on the carrier, the ligand and the acid is not sacrificed and the stability can be maintained.

Proportion of the ligand (A2) such as the organic phosphine is, for example, about 0.1 to 1,000 mol, usually about 5 to 500 mol, preferably about 10 to 200 mol and more preferably about 15 to 100 mol, relative to 1 mol of the Group VIII metal source (A1). The ligand may typically be used in a proportion of about 10 to 100 mol, and preferably about 20 to 60 mol per mol of the metal source. When such ligand is used in a too much small proportion, the catalytic activity tends to be decreased. On the contrary, use of the ligand in an excess amount is apt to result in an economical disadvantage.

In regard to the acid (for instance, a proton acid as a proton source), the amount of such acid is, per mol of the Group VIII metal source, for example about 0.1 to 1,000 mol, usually about 5 to 500 mol, preferably about 10 to 200 mol and more preferably about 15 to 100 mol. Typical use is made of the acid in an amount of about 10 to 100 mol, specifically about 20 to 60 mol per mol of the metal source. Proportion of the ligand such as the organic phosphine relative to 1 mol of the acid is, for instance, about 0.01 to 50 mol, usually about 0.1 to 50 mol, preferably about 0.2 to 20 mol and more preferably about 0.5 to 5 mol.

The amount of the electron donative compound is, for example, about 1 to 100,000 mol, preferably about 5 to 50,000 mol and more preferably about 10 to 10,000 mol, relative to 1 mol of the Group VIII metal source. Such electron donative compound may frequently be used in a proportion of about 10 to 10,000 mol (for example about 50 to 7,000 mol), and particularly about 100 to 5,000 mol per mol of the Group VIII metal source. The electron donative compound may be used as a reaction solvent, and in such a case, an excess amount of the electron donative compound relative to 1 mol of the Group VIII metal source may be sufficient. When the electron donative compound is not used as the reaction solvent, the proportion of the compound is typically about 2 to 200 mol, preferably about 5 to 100 mol and more preferably about 10 to 50 mol per mol of the Group VIII metal source. The electron donative compound may practically be used as the reaction solvent.

In a catalytic system where a Group VIII metal source as a catalytic active component is not supported on a carrier, use of a heterogeneous catalytic system containing the catalytic active component in a metal form (state) may sometimes result in an insufficient catalytic activity with decreasing the catalytic activity in a short period. When using a heterogeneous catalytic system containing a Group VIII metal compound, in some cases, the catalytic activity may gradually be decreased or sacrificed in the course of the use for some period or some times. Typically, such catalytic system containing a palladium source tends to result in significant deactivation of the catalyst, as mentioned above, although having comparatively high initial activity.

To the contrary, the catalytic system (A) of the present invention has, in spite of being a heterogeneous catalytic system, a high catalytic activity in carbonylation of an unsaturated hydrocarbon. Further, according to such catalytic system, high catalytic activity and long catalyst life can be obtained even when the Group VIII metal source is in a metallic form (a simple substance). Moreover, even if containing a palladium source as the Group VIII metal source, the catalytic system has meritoriously high stability, and high catalytic activity can be maintained or sustained for a long period of time. Thus, the catalyst can be used for a long time or repeatedly without activating treatment. Accordingly, the catalytic system (A) is useful for carbonylation of an acetylenic or olefinic (or ethylenic) unsaturated compound.

The catalytic system (B) of the present invention is now described in detail.

The catalytic system (B) of the present invention comprises (B1) a Group VIII metal source of Periodic Table of the Elements other than palladium. Such Group VIII metal element includes, for example, iron, ruthenium, osmium, cobalt, rhodium, iridium, nickel and platinum. Meanwhile, on or after the year of 1990, the elements are classified into, in Periodic Table of the Elements, the Group 8 elements (Fe, Ru, Os), the Group 9 elements (Co, Rh, Ir) and the Group 10 elements (Ni, Pt). Preferred example of the element includes rhodium, cobalt, nickel and platinum, and platinum can advantageously be used among others. The oxidation number of the element may be selected according to the species of the element and is not restricted. By way of illustration, platinum frequently has an oxidation number of 0, +2, +4 or others.

The Group VIII metal source (B1) may be in a metallic form or state, or, preferably, a compound of the Group VIII element.

Example of the compound of the Group VIII element includes the inorganic acid salt, the organic acid salt, the halogenated compound and the complex (or complex salt) as exemplified in the explanation of the catalytic compound (A). As the ligand for constituting such complex, there may be mentioned those as mentioned in the explanation of catalytic system (A). One or more of the same or different species of these ligands may be coordinated in the complex or complex salt.

As practical example of the complex or complex salt, there may be mentioned a platinum complex or complex salt including a dibenzylideneketoneplatinum such as dibenzylideneacetoneplatinum, dibenzylideneacetylacetoneplatinum and dibenzylideneacetophenoneplatinum; dicyclooctadieneplatinum, dichlorobis(triphenylphosphine) platinum, tetrakis (triphenylphosphine)platinum, bis (triphenylphosphine) platinum acetate, bis (triphenylphosphine)platinum sulfate and hexachloroplatinic (IV) acid; and a complex or complex salt of the Group VIII element corresponding to these complexes or complex salts.

The catalyst containing the Group VIII element other than palladium shows, typically in a homogeneous catalytic system, a significantly different behavior or action from a palladium catalyst. By way of illustration, a catalytic system comprising a palladium-catalyst and a triarylphosphine (triphenylphosphine) demonstrates a comparatively high catalytic activity, but addition of a tertiary amine such as pyridine remarkably decrease or sacrifice the catalytic activity in carbonylation of an olefin [Japanese Patent Application Laid-open No. 215852/1992 (JP-A-4-215852)].

On the other hand, in the catalytic system comprising an organic phosphine, when use is made of the other Group VIII metal source than palladium (for example, a platinum catalyst) in lieu of such palladium catalyst, addition of a tertiary amine significantly improve or enhance the activity and stability of the catalyst, and in such catalytic system, the catalytic activity can hardly be manifested without coexistence of the tertiary amine. These are features contrary to a conventional catalytic system containing a palladium catalyst. Further, similar results, namely significantly high activity and stability of the catalyst can be obtained by the use of an electron donative compound having a specific electron donability, typically a basic compound among them, even when such tertiary amine is not employed.

The catalytic system (B) comprises a ligand (B2). The ligand (B2) shown by the formula (Ib) may frequently be different from the ligand which constitutes the compound (complex) of the Group VIII metal as mentioned above. Usually, the ligand (B2) of the formula (Ib) comprises at least one phosphorus atom, arsenic atom or antimony atom, and can be coordinated to the Group VIII element. These ligands may be used singly or in combination.

The ligand (B2) as shown by the formula (Ib) does not contain a nitrogen-containing heterocyclic group, and thus is not a special or unusual compound. Therefore, the ligand (B2) of the catalytic system (B) can easily be prepared or be available.

In the formula (Ib), as examples and preferred examples of the alkyl group, the alkenyl group, the alkynyl group, the cycloalkyl group and the aryl group, and substituents which they may have, there may be mentioned those as exemplified in the explanation of the ligand (A2) of the catalytic system (A).

In the formula (Ib), A may preferably be a phosphorus atom or an arsenic atom, typically a phosphorus atom.

Preferred example of the ligand (B2) includes an organic phosphorus compound, an organic arsenic compound and an organic antimony compound, typically an organic phosphine and an organic arsine, and specifically an organic phosphine. The organic phosphine may be whichever of a primary phosphine (for example, methylphosphine, ethylphosphine, propylphosphine, isopropylphosphine, isobutylphosphine, isoamylphosphine, phenylphosphine, cyclohexylphosphine and so on), a secondary phosphine (for instance, dimethylphosphine, diethylphosphine, diisopropylphosphine, di-n-butylphosphine, diisoamylphosphine, diphenylphosphine, dicyclohexylphosphine and the like) or a tertiary phosphine. The organic arsine may also be whichever of a primary arsine, a secondary arsine or a tertiary arsine. Preferred example of such organic phosphine and organic arsine include a tertiary phosphine and a tertiary arsine.

In such organic phosphine, $R^1$ to $R^3$ are respectively the alkyl group, the alkenyl group, the alkynyl group, the cycloalkyl group or the aryl group, each of which may have a substituent. Typically preferred organic phosphine is a compound of the formula (Ib) where at least one of $R^1$ to $R^3$ is an aryl group such as phenyl group or a substituted phenyl group. In addition to such aryl group, the alkylene group which is formed by $R^2$ and $R^3$ is also preferable.

As preferred examples of the organic phosphine (tertiary organic phosphine), there may be mentioned (i) the optionally substituted triarylphosphines, (ii) the mono $C_{1-10}$ alkyl-di-arylphosphines, (iii) the di-$C_{1-10}$ alkyl-monoarylphosphines, (iv) the tri-$C_{1-10}$ alkylphosphines, (v) the mono-$C_{4-10}$ cycloalkyl-diarylphosphines, (vi) the di-$C_{4-10}$ cycloalkyl-monoarylphosphines, (vii) the tri-$C_{4-10}$ cycloalkylphosphines and (ix) other phosphines as exemplified in the explanation of the catalytic system (A).

As the ligand, an arsenic compound (specifically a tertiary organic arsine) and an antimony compound (typically a tertiary organic stibine) can also advantageously be employed.

The catalytic system (B) comprises, as the electron donative compound (B3), a compound having an electron donability ΔvD of not less than 2. The definition of the electron donability ΔvD may also be referred to the explanation of the catalytic system (A) as above.

Examples and preferred examples of the electron donative compound include those exemplified in the catalytic system (A).

Preferred example of the electron donative compound includes a basic compound such as the amine, the imide and the amide. Typically, when use is made of such basic compound (especially, a secondary amine and a tertiary amine) in combination with (B1) the Group VIII metal source except for palladium, the catalytic activity can significantly be improved or enhanced in many cases. Therefore, the catalytic system (B) may preferably comprise a basic compound selected from the group consisting of the amine, the imide and the amide. Further, combination use of these basic compounds with the ether and/or the ester may occasionally increase or enhance the transformation rate and the selectivity of the reaction.

In the catalytic system (B) of the present invention, a suitable combination of the ligand (B2) and the electron donative compound (B3) may be used according to the species of the metal source (B1). For example, even when a combination of (B1) the Group VIII metal source other than palladium and the organic phosphine as the ligand (B2) is employed, the stability and activity of the catalyst are not sacrificed or decreased regardless of the species of such organic phosphine. Accordingly, the organic phosphine can be used in a suitable combination with the compound (B3) having an electron donability ΔvD of not less than 2. By way of illustration, in the catalytic system comprising the triarylphosphine as the organic phosphine, the combination use of an nitrogen-containing compound or a basic compound (for instance, the amine compound such as pyridine or its derivative) can markedly improve or increase not only the stability but also the activity of the catalyst.

The catalytic system (B) of the present invention may further contain (B4) an acid. As such acid and preferred examples thereof, the similar acids and preferred examples to the catalytic system (A) can be mentioned.

The catalytic system (B) of the present invention may be whichever of a homogeneous catalyst or a heterogeneous catalyst. In the use for a liquid phase reaction, the catalytic system may generally be a homogeneous system. If necessary, the catalytic system (B) may comprise or form a solid catalyst wherein the catalytic component is supported on a carrier such as an activated carbon, alumina, silica and others. The proportions of each components can be selected, according to the species of each of the catalytic components, within a range insofar as the activity and stability of the catalyst are not adversely affected.

The ratio of the ligand (B2) such as the organic phosphine is, for instance, about 0.1 to 1,000 mol, preferably about 0.5 to 500 mol, more preferably about 1 to 100 mol and frequently about 1 to 50 mol, relative to 1 mol of the Group VIII metal source (B1). The proportion of the acid (for example a proton acid as a proton source) is, relative to 1 mol of the Group VIII metal source (B1), about 0.1 to 1,000 mol, preferably about 1 to 500 mol, more preferably about 5 to 250 mol, and for still better results, about 1 to 100 mol.

The amount of the ligand (B2) such as the organic phosphine relative to 1 mol of the acid (B4) such as the proton acid may not be restricted, and is, for example, about 0.01 to 50 mol, preferably about 0.02 to 10 mol, and more preferably about 0.05 to 5 mol. Frequently, the ligand may be used in a proportion of about 0.03 to 3 mol per mol of the acid.

The proportion of the electron donative compound (B3) is, for example, about 1 to 100,000 mol, preferably about 5 to 50,000 mol and more preferably about 10 to 10,000 mol, relative to 1 mol of the Group VIII metal source. Such electron donative compound may frequently be used in a proportion of about 10 to 10,000 mol (for example about 50 to 7,000 mol), and particularly about 100 to 5,000 mol per mol of the Group VIII metal source. The electron donative compound (B3) may be used as a reaction solvent, and in such a case, an excess amount of the electron donative compound relative to 1 mol of the Group VIII metal source may be sufficient. When the electron donative compound is not used as the solvent, the proportion of the compound is typically about 2 to 200 mol, preferably about 5 to 100 mol and more preferably about 10 to 50 mol per mol of the Group VIII metal source. The electron donative compound is practically used as the reaction solvent.

The catalytic system (B) of the present invention can show or perform high activity and stability in the carbonylation of an unsaturated hydrocarbon, and thus is useful in carbonylation of an acetylenic or olefinic unsaturated compound.

According to the method of the present invention, an acetylenic or olefinic unsaturated compound is allowed to react with carbon monoxide in the presence of the catalytic system (A) or (B) to give a carbonylation reaction product.

The acetylenic or olefinic unsaturated compound may preferably be an asymmetric acetylenic or olefinic compound, and more preferably be an α-acetylenic compound, an α-olefinic compound or an allene compound. The acetylenic compound (acetylene series compound) has usually about 2 to 30, preferably about 2 to 20, and particularly about 2 to 10 carbon atoms. The olefinic compound and the allene compound may have, for example, about 2 to 30, preferably about 2 to 20, and typically about 2 to 10 carbon atoms. These unsaturated compounds include an alkyne, an alkene (olefin), a cycloalkene, a cycloalkadiene and a bridged unsaturated hydrocarbon, each of which may have a substituent. The unsaturated hydrocarbon may have both of a double bond and a triple bond, or two or more of double bonds in a molecule.

The unsaturated compound may have a various substituent. Example of such substituent includes a halogen atom such as fluorine, chlorine, bromine and so on; a $C_{1-10}$ cycloalkyl group such as cycloheptyl, cyclohexyl and cyclooctyl groups; an aryl group such as phenyl and naphthyl groups; an aralkyl group such as benzyl and phenethyl groups; a cyano group; an acyl group having about 1 to 7 carbon atoms such as formyl, acetyl, propionyl, butyryl, isobutyryl, valeryl, isovaleryl and pivaloyl groups; an acyloxy group having, in the alkyl moiety, about 1 to 6 carbon atoms such as acetoxy group; a hydroxyl group; an alkoxy group having about 1 to 6 carbon atoms such as methoxy, ethoxy, propoxy, butoxy and t-butoxy groups; a haloalkyl group such as trifluoromethyl and trichloromethyl groups; a haloalkoxy group such as trifluoromethoxy and trichloromethoxy groups; a carboxyl group; an alkoxycarbonyl group having, in the alkoxy moiety, about 1 to 6 carbon atoms; an amino group and an N-substituted amino group such as a monoalkylamino group and a dialkylamino group; an amide group and an N-substituted amide group such as acetamide group and the like.

As example of the alkyne, there may be mentioned acetylene, propyne, 1-butyne, 2-butyne, 1-pentyne, 1-hexyne, 1-heptyne, 1-octyne, 2-octyne, 4-octyne, 1,7-octadiyne, 5-methyl-3-heptyne, 4-propyl-2-pentyne, 1-nonyne, phenylacetyne, benzylethyne and cyclohexylethyne.

The alkene includes, for example, ethylene, propylene, phenylethylene, 1-butene, 2-butene, 1-pentene, 3-methylpentene-1, 4-methylpentene-1,1-hexene, 1-heptene, 1-octene, 2-octene, 4-octene, allene, cyclohexene and norbornadiene.

As carbon monoxide, whichever of pure carbon monoxide or a carbon monoxide diluted with an inert gas such as nitrogen, helium, argon, carbon dioxide and others may be employed.

The unsaturated compound may be carbonylated individually, or in the presence of another reactant such as a nucleophilic compound having a hydrogen or a hydrogen atom which can be left in the reaction (active hydrogen). Example of the nucleophilic compound having a hydrogen atom capable of releasing includes a compound having a hydroxyl group such as an alcohol, water and a carboxylic acid. The alcohol may also include a silanol.

The alcohol may be whichever of an aliphatic, alicyclic, aromatic alcohol or a phenol, and of a monohydric or polyhydric alcohol. Such alcohol may have one or more of substituents other than a hydroxyl group among the substituents as exemplified in the explanation of the unsaturated compound.

As the monohydric alcohol, there may be mentioned, for instance, an aliphatic alcohol such as methanol, ethanol, 1-propanol, 2-propanol, 1-butanol, 2-butanol, 1-methylpropan-1-ol, 2-methylpropan-1-ol, 2-methylpropan-2-ol, 1-hexanol, 1-octanol, 2-ethylhexanol, stearyl alcohol, allyl alcohol, crotyl alcohol and propargyl alcohol; an alicyclic alcohol such as cyclopentanol, cyclohexanol 4-methylcyclohexanol, cyclohexen-1-ol, cycloheptanol, cyclooctanol and borneol; and an aromatic alcohol such as benzyl alcohol, salicyl alcohol, benzhydrol and phenethyl alcohol. The phenol includes, for example, phenol, an alkylphenol, resorcinol, catechol and 2,2-bis(4-hydroxyphenyl)propane.

Example of the polyhydric alcohol includes ethylene glycol, propylene glycol, diethylene glycol, polyethylene glycol, dipropylene glycol, polypropylene glycol, trimethylene glycol, tetramethylene glycol, 1,6-hexanediol, glycerol, trimethylolpropane(2,2-bishy-droxymethyl-1-butanol), pentaerythritol, 1,2-cyclohexanediol, 1,4-cyclohexanediol, a carbohydrate (a monosaccharide, an oigosaccharide, a polysaccharide) such as glucose, fructose, mannose, galactose, saccharose, aldohexose, aldopentose, altrose, allose, talose, gulose, idose, ribose, arabonose, xylose, lyxose, erythrose, threose and cellulose.

Preferred example of the alcohol includes a monohydric alcohol having about 1 to 20, particularly about 1 to 10, and among them about 1 to 5 carbon atoms. An aliphatic saturated alcohol may typically used as the alcohol.

As example of the carboxylic acid, an aliphatic carboxylic acid such as formic acid, acetic acid, propionic acid, n-butyric acid, isobutyric acid, pivalic acid, valeric acid, caproic acid, caprylic acid, capric acid, lauric acid, myristic acid, palmitic acid and stearic acid; an alicyclic carboxylic acid such as cyclohexanecarboxylic acid; an aromatic carboxylic acid such as benzoic acid, phthalic acid, isophthalic acid and terephthalic acid; and an unsaturated carboxylic acid such as acrylic acid, methacrylic acid, propionic acid, crotonic acid, maleic acid, fumaric acid, citraconic acid, mesaconic acid and oleic acid. An aliphatic carboxylic acid, preferably that having about 2 to 20, and more preferably about 2 to 18 carbon atoms, and in particular an aliphatic carboxylic acid having about 2 to 10 carbon atoms may be used as the carboxylic acid, typically speaking.

An alcohol or water may frequently be used as the nucleophilic compound having a hydrogen atom which can be left in the reaction.

In the carbonylation reaction, a compound corresponding to the olefinic unsaturated compound and the acetylenic unsaturated compound can be produced according to species of the reactant. By way of illustration, when water is employed as the reactant, a corresponding carboxylic acid and an unsaturated carboxylic acid such as an $\alpha,\beta$-unsaturated carboxylic acid are produced by carbonylation of the olefinic unsaturated compound and the acetylenic unsaturated compound. The use of an alcohol results in production of an ester corresponding to the carboxylic acid and the unsaturated carboxylic acid. Further, in the case of using a carboxylic acid, an acid anhydride corresponding to the carboxylic acid and the unsaturated carboxylic acid is produced.

For example, when use is made of ethylene as the olefinic unsaturated compound, and methanol or water as the reactant (nucleophilic compound), methyl propionate or propionic acid can be produced by reacting with carbon monoxide. By allowing allene as the olefinic unsaturated compound and methanol or water as the reactant (nucleophilic compound) to react with carbon monoxide, methyl methacrylate or methacrylic acid may be obtained. Methyl methacrylate or methacrylic acid may also be produced by using propyne as the acetylenic compound and methanol or water as the reactant (nucleophilic compound) to react with carbon monoxide.

Thus, according to the method of the present invention, species of the reactant may be selected depending on the objective compound, and is frequently water, an alcohol or an organic carboxylic acid.

Proportions of each components in the carbonylation may be selected within a wide range. By way of exemplification, the amount of the catalytic system is, in terms of atomic metal of the Group VIII metal source, about $1\times10^{-6}$ to $2\times10^{-1}$ mol, preferably about $1\times10^{-5}$ to $1\times10^{-1}$ mol and frequently about $1\times10^{-4}$ to $1\times10^{-2}$ mol, relative to 1 mol of the acetylenic or olefinic unsaturated compound. The proportion of the catalytic system (A) or (B) may also selected from within the range about 0.01 to 15% by weight, preferably about 0.1 to 10% by weight, and frequently about 0.5 to 8% by weight relative to the acetylenic or olefinic unsaturated compound.

When the catalytic system (A) is employed, the proportion of carbon monoxide is, for example per mol of the acetylenic or olefinic unsaturated compound, about 0.1 to 100 mol, preferably about 1 to 80 mol, and more preferably about 1.5 to 50 mol (for instance, about 1.5 to 5 mol). The reactant (nucleophilic compound) may be used, for instance, in an amount of about 0.1 to 100 mol, preferably about 0.1 to 80 mol, and more preferably about 1 to 50 mol (for example, about 1.5 to 5 mol), relative to 1 mol of the acetylenic or olefinic unsaturated compound. When water is employed as the reactant, the amount thereof may be about 0.5 to 10 mol per mol of the unsaturated compound.

As to the catalytic system (B), the ratio of carbon monoxide is, for example, about 0.1 to 100 mol (e.g. about 1 to 20 mol), preferably about 0.8 to 10 mol (for instance, about 1.2 to 10 mol), and more preferably about 1.0 to 5 mol (e.g. about 1.5 to 5 mol), per mol of the acetylenic or olefinic unsaturated compound. Such carbon monoxide may frequently be used in an excess amount (for example about 1 to 20 mol) relative to 1 mol of the acetylenic or olefinic unsaturated compound. The ratio of the reactant (the nucleophilic compound) is, for instance per mol of the acetylenic or olefinic unsaturated compound, about 0.1 to 100 mol (e.g. about 1.0 to 20 mol), preferably about 0.8 to 10 mol (for example, about 1.2 to 10 mol) and more preferably about 1.0 to 5 mol (for instance, about 1.5 to 5 mol). When water is employed as the reactant, the amount of such reactant may be about 0.5 to 10 mol relative to 1 mol of the unsaturated compound.

Meanwhile, the reactant may also be used as a reaction solvent.

The reaction (carbonylation) may be carried out in an inert organic solvent. As example of such organic solvent, there may be mentioned an aliphatic hydrocarbon such as hexane and octane; an aromatic hydrocarbon such as benzene; a halogenated hydrocarbon such as chloroform, dichloromethane, carbon tetrachloride and chlorobenzene; and a mixture of these solvents. Where the electron donative compound or the reactant is used as a solvent, the above-mentioned organic solvent is not necessarily employed.

The carbonylation reaction may typically be conducted at a temperature of, for instance, about 10 to 250° C. (e.g. about 10° to 200° C.) and preferably about 25 to 200° C., and under a pressure of about 1 (atmospheric) to 150 atm and preferably about 1 to 100 atm. The reaction may be carried out in accordance with a conventional method such as a batch method, semi-batch method or continuous method, and in a liquid phase or in a gas (gaseous) phase. Since the catalytic systems (A) and (B) have high stability, the reaction is practically conducted in a liquid phase. In particular, the catalytic system (B) may practically be used as a homogeneous system in a liquid phase. Meanwhile, the above mentioned catalytic systems (A) and (B) may be used singly or in a suitable combination.

After completion of the reaction, the reaction product(s) can easily be separated and purified according to a conventional technology such as a separating means including filtration, concentration, distillation, extraction, crystallization, recrystallization and column chromatography, or a combination of these technologies.

Since comprising the Group VIII metal source supported on the carrier as the catalytic component, the catalytic system (A) of the present invention has high catalytic activity and excellent stability even thought being a heterogeneous catalytic system, and thus can maintain high catalytic activity in a carbonylation reaction. Therefore, when use is made of the catalytic system (A) for carbonylation of an acetylenic or olefinic unsaturated compound, a carbonylation product such as a carboxylic acid or an ester of a carboxylic acid can stably be produced in a stable liquid phase with high transformation rate and selectivity for a long period. Such carbonylation can be conducted without activation of the catalyst. Further, an α,β-ethylenic unsaturated carboxylic acid or a derivative thereof can be produced with high transformation rate and selectivity as well as high stability.

According to the catalytic system (B) of the present invention which comprises the Group VIII metal source except for palladium and the specific electron donative compound as the catalytic components, the stability of the catalytic system can be improved or enhanced without the use of a special phosphine, and high catalytic activity can be obtained in a carbonylation reaction. Therefore, with utilizing the catalytic system (B) for carbonylation of an acetylenic or olefinic unsaturated compound, a carbonylated product such as a carboxylic acid or a carboxylic acid ester can be obtained in a stabilized liquid phase with high transformation rate and selectivity. Moreover, an α,β-ethylenic unsaturated carboxylic acid or a derivative thereof can be produced with high transformation rate and selectivity.

The following examples are merely intended to illustrate the present invention in further detail and should not be construed as defining the scope of the invention.

EXAMPLES

In the following examples, the term "part" means "part by weight".

Example 1

To 100 parts of acetone and 0.03 part of concentrated hydrochloric acid (an aqueous solution containing about 35% or more of hydrogen chloride) was added 1.77 part of palladium chloride for dissolving. A granular activated carbon [trade name: Shirasagi C, manufactured by Takeda Chemical Industries Co., Ltd.; specific surface area of 1,200 m²/g; pore volume of 0.53 ml/g; mean pore size of 17 Å](100 parts) was dipped in the resultant solution to adsorb palladium chloride on the activated carbon.

A nitrogen-substituted stainless-steel autoclave (inner volume of 30 ml) was charged with palladium chloride-supporting activated carbon prepared above in an amount of $5 \times 10^{-6}$ mol in terms of palladium chloride, and with $2 \times 10^{-4}$ mol of triphenylphosphine, $2 \times 10^{-4}$ mol of methanesulfonic acid, 4 ml of methanol and 0.1 g of methylacetylene, in turn. The autoclave was introduced with carbon monoxide up to a pressure of 60 Kg/cm², and was sealed. The reaction was conducted under heating and stirring at 60° C. for 2 hours.

The reaction product was analyzed by gas chromatography. As a result, the mean transformation rate of methylacetylene was 142 mol/hr per gram atom of palladium, and the methylacetylene-based selectivity for the product methyl methacrylate was 80%.

Example 2

The reaction solution obtained in Example 1 was concentrated under reduced pressure to remove the produced methyl methacrylate and unreacted methanol and methylacetylene. To the residual concentrate, were added methanol and methylacetylene in the same proportions as Example 1. Carbon monoxide was introduced into the autoclave and the reaction was conducted in the same manner as Example 1.

A series of procedures of such concentration of the reaction mixture, charging of the raw materials, and the reaction was repeated five (5) times. The results are set forth in Table 1. In the following Tables, the term "Transformation rate" means the mean transformation rate (mol per hour) of methylacetylene per gram atom of palladium. The term "Selectivity" shows the methylacetylene-based selectivity (%) for the product methyl methacrylate. As apparent from Table 1, although the catalyst was used repeatedly, the transformation rate of methylacetylene and the selectivity for methyl methacrylate were scarcely changed or sifted.

TABLE 1

| Repeating times | Transformation rate (mol/hr) | Selectivity (%) |
|---|---|---|
| 1 | 141 | 81 |
| 2 | 139 | 82 |
| 3 | 140 | 81 |
| 4 | 138 | 82 |
| 5 | 139 | 80 |

Comparative Example 1

The procedure of Example 1 was repeated except that palladium chloride which was not supported on a carrier was used instead of palladium chloride supported on the activated carbon. Resultantly, the fed methylacetylene was transformed to methyl methacrylate at an average transformation rate of 145 mol/hr per gram atom of palladium, and the methylacetylene-based selectivity for methyl methacrylate was 81%. By analyzing the reaction mixture after completion of the reaction, it was found that a part of palladium chloride was reduced to cause a precipitate of metallic palladium.

Comparative Example 2

The series of procedures described in Example 2 were repeated five times in the same manner as Example 2, except for using the reaction mixture obtained in Comparative Example 1 instead of the reaction mixture obtained in Example 1. The results are shown in Table 2. As clearly shown in Table 2, when the catalyst was utilized repeatedly, the transformation rate of the methylacetylene was significantly decreased.

TABLE 2

| Repeating times | Transformation rate (mol/hr) | Selectivity (%) |
|---|---|---|
| 1 | 112 | 79 |
| 2 | 98 | 80 |
| 3 | 83 | 78 |
| 4 | 61 | 78 |
| 5 | 53 | 76 |

Example 3

To a diluted aqueous solution of hydrochloric acid containing 1.77 part of palladium chloride was added 100 parts of γ-alumina [trade name: Neospeed, manufactured by Mizusawa Chemical Co., Ltd., Japan; specific surface area of 200 m²/g; pore volume of 0.40 ml/g; mean pore size of 80 Å], and γ-alumina was dipped in palladium chloride with stirring. To the dipped γ-alumina, were added 5 parts of an aqueous solution of formalin and 100 parts of a 1N aqueous solution of sodium hydroxide to reduce palladium chloride. The resultant mixture was filtrated, and the residue was washed with water and dried to give a metallic palladium-supported catalyst.

The reaction was conducted in the same manner as Example 1 except that, instead of the palladium chloride supported on the activated carbon, the metallic palladium supported on γ-alumina was used in an amount of $5 \times 10^{-6}$ mol in terms of metallic palladium, and that $2 \times 10^{-4}$ mol of 2,6-bis(diphenylphosphino)pyridine was employed in lieu of triphenylphosphine. As a result, the mean transformation rate of methylacetylene was 245 mol/hr per gram atom of palladium, and methyl methacrylate was produced with a methylacetylene-based selectivity of 87%.

Thus, the series of the procedures, that is, the concentration of the reaction mixture, charging of the raw materials and the reaction, was repeated 10 times in the same manner as Example 2. Resultantly, even after the procedure was repeated 10 times, methylacetylene was transformed to methyl methacrylate at a mean transformation rate of 239 mol/hr per gram atom of palladium, and the catalytic activity was scarcely decreased.

Comparative Example 3

The reaction was conducted in the similar manner as Example 3 except for using palladium black which was not supported on a carrier in lieu of the metallic palladium supported on γ-alumina. As a result, the mean transformation rate for methylacetylene was 112 mol/hr per gram atom of palladium and the methylacetlene-based selectivity for methyl methacrylate was 83%.

Then, the series of the procedures as in Example 2, namely, concentration of the reaction mixture, the charging of the raw materials and the reaction, was repeated 10 times. After ten-time repetition of the procedures, the mean transformation rate of methylacetylene was remarkably decreased to 18 mol/hr per gram atom of palladium, and the selectivity for methyl methacrylate was decreased to 43%.

Example 4

The procedure of Example 1 was followed except that triphenylarsine was employed instead of triphenylphosphine. Methylacetylene was transformed to methyl methacrylate at a mean transformation rate of 23 mol/hr per gram atom of palladium, and the methylacetylene-based selectivity for the product methyl methacrylate was 53%.

After repeating the series of procedures of concentration of the reaction mixture, charging of the raw material and the reaction five times in the same manner as Example 2, the mean transformation rate of methylacetylene and the methylacetylene-based selectivity for methyl methacrylate changed scarcely.

Example 5

A stainless steel-autoclave (inner volume of 300 ml) was charged with 0.25 mmol of dibenzylideneacetone-platinum (0), 1 mmol of triphenylphosphine, 10 mmol of methanesulfonic acid, 48 g (609 mmol) of pyridine and 20 g (624 mmol) of methanol. Propyne (300 mmol) and carbon monoxide (600 mmol) were introduced into the autoclave after expelling air therefrom. The autoclave was sealed and heated, and thus the reaction was conducted under a pressure of 60 atm and at a temperature of 100° C. for 1 hour.

By analyzing the reaction product(s) using gas chromatography, propyne was transformed to methyl methacrylate at a transformation rate of 35.6% and with a selectivity for methyl methacrylate of 96.9%. As for the reaction mixture after completion of the reaction, no precipitate was observed and the mixture was homogeneous.

Comparative Example 4

The reaction was carried out in the same manner as Example 5 except for using methanol as the reactant in lieu of pyridine as the solvent. As a result, methyl methacrylate in a trace amount was detected.

Comparative Example 5

A stainless steel autoclave (300 ml in inner volume) was charged with 0.05 mmol of palladium (II) chloride, 2 mmol of triphenylphosphine, 2 mmol of methanesulfonic acid, 0.2 g (2 mmol) of pyridine and 3.96 g (124 mmol) of methanol. After expelling air from the autoclave, 300 mmol of propyne and 600 mmol of carbon monoxide were introduced thereto. The autoclave was sealed and heated, and reaction was conducted at 60 atm and 63° C. for 1 hour.

The reaction products were analyzed by gas chromatography. Resultantly, the transformation rate of propyne was so little as 3.7%, and methyl methacrylate was produced with a selectivity of 52.7 %. When examining the resultant reaction mixture, precipitates of metallic palladium due to metalation of palladium were observed.

Comparative Example 6

The reaction procedure of Comparative Example 5 was repeated except that 0.2 g of methanol (total amount of 4.16 g) was used instead of 0.2 g of pyridine to give methyl methacrylate with a selectivity of about 80%. The transformation rate of propyne was about 30%. In the reaction mixture after completion of the reaction, precipitates of metallic palladium due to metalation were produced.

Example 6

With 2.5 mmol of dibenzylideneacetoneplatinum (0), 10 mmol of triphenylphosphine, 10 mmol of methanesulfonic acid, 48 g (609 mmol) of pyridine and 20 g (624 mmol) of methanol, was charged a stainless steel autoclave (300 ml in inner volume). Air was expelled from the autoclave and 300 mmol of propyne and 600 mmol of carbon monoxide were introduced to the autoclave. After sealing, the autoclave was heated and the reaction was carried out at 60 atm and at 100° C. for 30 minutes, and the resulting products were analyzed by gas chromatography.

As a result, methyl methacrylate was produced with a selectivity of 99.0%, and the transformation rate of propyne was 98.7%. Further, in the resultant reaction mixture, no precipitate was observed and the mixture was homogeneous.

Example 7

A 300 ml-stainless steel autoclave (as inner volume) was charged with 0.25 mmol of dibenzylideneacetoneplatinum (0), 10 mmol of triphenylphosphine, 10 mmol of methanesulfonic acid, 30 g of α-picoline and 20 g (624 mmol) of methanol. After expelling air from the autoclave, were introduced 300 mmol of propyne and 600 mmol of carbon monoxide thereto, and the autoclave was sealed and heated to conduct the reaction at 60 atm and at a temperature of 100° C. for 1 hour.

The resultant products were analyzed by gas chromatography. Resultantly, propyne was transformed to methyl methacrylate with a transformation rate of 14.0%, and the selectivity for methyl methacrylate was 95.3%. Further, no precipitate was observed in the reaction mixture, thus the mixture was homogeneous.

Example 8

The reaction procedure of Example 5 was repeated except for using 30 g of 2,6-lutidine instead of 48 g of pyridine, and using triphenylphosphine in an amount of 10 mmol to give methyl methacrylate with a selectivity of 91.9% and with a transformation rate of propyne of 7.7%. As a result of investigating the reaction mixture, the mixture was observed to be homogeneous without any precipitate.

Example 9

By using 30 g of 1-methylimidazole in lieu of 48 g of pyridine, and employing triphenylphosphine in a proportion of 10 mmol, methyl methacrylate was obtained in the same manner as Example 5 with a selectivity of 89.5%. The transformation rate of propyne was 11.5%. In the reaction mixture, no precipitate was produced and the mixture was homogeneous.

Example 10

The procedure of Example 5 was repeated except that 30 g of anisole was used instead of 48 g of pyridine, and the amount of triphenylphosphine was changed to 10 mmol to give methyl methacrylate with a selectivity of 82.0%. The fed propyne was transformed to methyl methacrylate at a transformation rate of 4.0%. The reaction mixture was homogeneous accompanying with no precipitate.

Example 11

Methyl methacrylate was obtained with a selectivity of 71.4% in the same manner as Example 5 except for employing 30 g of xylene in lieu of 48 g of pyridine and using triphenylphosphine in a proportion of 10 mmol. The transformation rate of propyne was 8.6%. By analyzing the reaction mixture, no precipitate was observed and the mixture was homogeneous.

Example 12

With the use of 5 mmol of transbis(1,2-diphenyl) phosphinomethylcyclobutane instead of 1 mmol of triphenylphosphine, the reaction was conducted in the similar manner as Example 5, and propyne was transformed at a rate of 21.9% to methyl methacrylate. The selectivity for the product methyl methacrylate was 90.5%. The reaction mixture was homogeneous without any precipitate.

Comparative Example 7

A stainless steel autoclave (300 ml in inner volume) was charged with 0.25 mmol of dibenzylideneacetoneplatinum (0), 1 mmol of 2-pyridylphenylphosphine, 10 mmol of methanesulfonic acid and 68 g (2,122 mmol) of methanol. After expelling air from the autoclave, were introduced 300 mmol of propyne and 600 mmol of carbon monoxide to the autoclave. The autoclave was sealed and heated to carry out the reaction at 100° C. for 1 hour. By analysis of the resultant products with the use of gas chromatography, the transformation rate of propyne was 8% and methyl methacrylate was produced with a selectivity of 21%.

Example 13

The reaction procedure of Example 5 was repeated except for employing a reaction temperature of 120° C. to give methyl methacrylate with a selectivity of 98.6% and with a transformation rate of propyne being 48%. The reaction mixture was observed to be homogeneous with no precipitate.

Example 14

A stainless steel autoclave (300 ml in inner volume) was charged with 0.63 mmol of dibenzylideneacetoneplatinum, 1 mmol of triphenylphosphine, 10 mmol of sulfuric acid, 1.6 g (20.2 mmol) of pyridine, 38.4 g (384 mmol) of methyl crotonate and 20 g (624 mmol) of methanol. Propyne (300 mmol) and carbon monoxide (600 mmol) were introduced into the autoclave after expelling air therefrom. The autoclave was sealed and heated, and the reaction was carried out at 60 atm and 150° C. for 10 minutes.

By analyzing the reaction products with the use of gas chromatography, the fed propyne was transformed to methyl methacrylate at a transformation rate of 38.0%, and the selectivity for methyl methacrylate was 94.2%. In the reaction mixture, no precipitate was observed and the mixture was homogeneous.

Example 15

By using 0.63 mmol of dibenzylideneacetoneplatinum, 1 mmol of triphenylphosphine, 20 mmol of sulfuric acid, 9.5 g (120 mmol) of pyridine, 30.5 g (305 mmol) of methyl crotonate and 20 g (624 mmol) of methanol, the reaction was conducted in the same manner as Example 14. Resultantly, propyne was transformed to methyl methacrylate at a transformation rate of 41.4%, and the selectivity for methyl methacrylate was 99.7% The reaction mixture after completion of the reaction was homogeneous and no precipitate was observed.

Example 16

The reaction procedure of Example 14 was repeated except for using 0.65 mmol of dibenzylideneacetoneplatinum (0.02% by weight in terms of platinum), 1 mmol of triphenylphosphine, 3.6 g (0.1 mol) of hydrochloric acid, 40 g (506 mmol) of pyridine and 20 g (624 mmol) of methanol to give methyl methacrylate with a selectivity of 97.8%. The transformation rate of propyne was 46.7%. In investigating the reaction mixture, the mixture was homogeneous without any precipitate.

Example 17

By using 0.63 mmol (0.02% by weight in terms of platinum) of dibenzylideneacetoneplatinum, 1 mmol of triphenylphosphine, 10 mmol of methanesulfonic acid, 1.6 g (20.2 mmol) of pyridine, 38.4 g (384 mmol) of methyl crotonate and 20 g (624 mmol) of methanol, the reaction was carried out in the same manner as in Example 14. Propyne was transformed to methyl methacrylate at a transformation rate of 53.4%, and the selectivity for methyl methacrylate was 96.6%. The reaction mixture after completion of the reaction was homogeneous with no precipitate.

Example 18

Methyl methacrylate was produced with a selectivity of 89.6% in the same manner as Example 14, except that 0.63 mmol of dibenzylideneacetoneplatinum, 1 mmol of triphenylphosphine, 14 mmol of phosphoric acid, 1.6 g (20 mmol) of pyridine, 38.4 g (384 mmol) of methyl crotonate and 20 g (624 mmol) of methanol were employed. The transformation rate of propyne was 37.9%. By investigating the reaction mixture, no precipitate was observed, and the mixture was homogeneous.

Example 19

The reaction procedure of Example 14 was repeated except for employing 0.63 mmol of dibenzylideneacetoneplatinum, 1 mmol of triphenylphosphine, 10 mmol of sulfuric acid, 4.7 g (59 mmol) of pyridine, 35.3 g (327 mmol) of anisole and 20 g (624 mmol) of methanol to give methyl methacrylate with a selectivity of 97.9%. The transformation rate of propyne was 36.9%. In the reaction mixture, no precipitate was observed and the mixture was homogeneous.

Example 20

With the use of 0.63 mmol of dibenzylideneacetoneplatinum, 1 mmol of triphenylphosphine, 10 mmol of sulfuric acid, 40.0 g (400 mmol) of methyl crotonate and 20 g (624 mmol) of methanol, the reaction was conducted in the same manner as Example 14. Propyne was transformed at a transformation rate of 25.6% and methyl methacrylate was procured with a selectivity of 89.5%. By investigating the reaction mixture after completion of the reaction, the reaction mixture was observed to be homogeneous without any precipitate.

Example 21

Methyl methacrylate was obtained with a selectivity of 94.1% in the same manner as Example 14, except that 0.63 mmol of dibenzylideneacetoneplatinum, 1 mmol of triphenylphosphine, 10 mmol of sulfuric acid, 4.7 g (59 mmol) of pyridine, 35.3 g (218 mmol) of diethylene glycol dimethyl ether and 20 g (624 mmol) of methanol were used. The transformation rate of propyne was 51.5%. In the reaction mixture, no precipitate was observed and the reaction mixture was homogeneous.

Example 22

The reaction procedure of Example 14 was repeated except for employing 0.63 mmol of dibenzylideneacetoneplatinum, 1 mmol of triphenylphosphine, 10 mmol of methanesulfonic acid, 1.9 g (20 mmol) of β-picoline, 38.1 g (381 mmol) of methyl crotonate and 20 g (624 mmol) of methanol. As a result, propyne was transformed to methyl methacrylate at a transformation rate of 41.2%, and the selectivity for methyl methacrylate was 93.5%. By examining the reaction mixture, no precipitate was produced and the mixture was homogeneous.

Example 23

By using 0.63 mmol of dibenzylideneacetoneplatihum, 1 mmol of triphenylphosphine, 10 mmol of methanesulfonic acid, 1.7 g (16 mmol) of diethanolamine, 38.5 g (385 mmol) of methyl crotonate and 20 g (624 mmol) of methanol, methyl methacrylate was produced with a selectivity of 98.2% in the same manner as Example 14. The transformation rate of propyne was 51.2%. The reaction mixture after completion of the reaction was homogeneous without any precipitate.

Example 24

Methyl methacrylate was obtained with a selectivity of 74.5% in the same manner as Example 14, except that 0.63 mmol of dibenzylideneacetoneplatinum, 1 mmol of triphenylphosphine, 40 g (506 mmol) of pyridine and 20 g (624 mmol) of methanol were used. The transformation rate of propyne was 47.0%. In the reaction mixture, no precipitate was observed and the reaction mixture was homogeneous.

Example 25

The reaction procedure of Example 14 was repeated except for employing 0.65 mmol of dibenzylideneacetoneplatinum, 1 mmol of triphenylphosphine, 4.7 g (59 mmol) of pyridine, 40 g (370 mmol) of anisole and 20 g (624 mmol) of methanol. As a result, propyne was transformed to methyl methacrylate at a transformation rate of 24.0%, and the selectivity for methyl methacrylate was 99.6%. By examining the reaction mixture, no precipitate was observed and the mixture was homogeneous.

Example 26

By using 0.63 mmol of dibenzylideneacetoneplatinum, 1 mmol of triphenylphosphine, 10 mmol of methacrylic acid, 0.8 g (5 mmol) of dipyridine, 40.0 g (400 mmol) of methyl crotonate and 20 g (624 mmol) of methanol, methyl methacrylate was produced with a selectivity of 97.7% in the same manner as Example 14. The transformation rate of propyne was 47.3%. The reaction mixture after completion of the reaction was homogeneous without any precipitate.

Example 27

Methyl methacrylate was obtained with a selectivity of 95.5% in the same manner as Example 14, except that 0.63 mmol of chloroplatinic acid, 1 mmol of triphenylphosphine, 10 mmol of sulfuric acid, 1.6 g (20 mmol) of pyridine, 38.4 g (384 mmol) of methyl crotonate and 20 g (624 mmol) of methanol were used. The transformation rate of propyne was 17.8%. In the reaction mixture, no precipitate was observed and the reaction mixture was homogeneous.

Example 28

A stainless steel autoclave (inner volume of 300 ml) was charged with 2.5 mmol of dibenzylideneacetoneplatinum, 10 mmol of triphenylphosphine, 10 mmol of methanesulfonic acid, 45 g (569 mmol) of pyridine and 4.3 g (134 mmol) of methanol. After expelling air from the autoclave, 67 mmol of allene and 610 mmol of carbon monoxide were introduced thereto. The autoclave was sealed and heated to conduct the reaction at 60 atm and 100° C. for 1 hour.

As a result of analyzing the reaction products with the use of gas chromatography, allene was transformed to methyl methacrylate at a transformation rate of 48%, and the selectivity for methyl methacrylate was 95.5%. The reaction mixture after completion of the reaction was homogeneous without any precipitate.

Example 29

The reaction procedure of Example 5 was repeated except that diphenylbutanephosphine was used in lieu of triphenylphosphine, and that the reaction was carried out at a temperature of 150° C. for 10 minutes to give methyl methacrylate with a selectivity of 97.0% with the selectivity of propyne being 25%. In the reaction mixture, no precipitate was observed and the mixture was homogeneous.

Example 30

A flask was charged with 0.2 mmol of platinum (II) chloride, 10 mmol of triphenylphosphine, 23.92 mmol of pyridine and 141.16 mmol of anisole, and the flask was heated at 150° C. Resultantly, even after heating for 40 hours, no metal was deposited or precipitated and the catalytic system was maintained in homogeneity.

Comparative Example 8

The procedure of Example 30 was repeated except for employing 0.2 mmol of palladium acetate instead of 0.2 mmol of platinum (II) chloride to examine the stability of the catalytic system. As a result, a precipitate was observed from 20 minutes past after the initial of heating. By analyzing palladium concentration in the reaction mixture after 2-hour heating treatment, palladium was detected only in few ppm at most, and the majority of palladium was deposited or precipitated as metal. Thus, the catalytic system was extremely instable.

What is claimed is:

1. A catalytic system for carbonylation which is;
   (A) a catalytic system comprising (A1) a Group VIII metal source of Periodic Table of the Elements, said metal source being supported on a carrier, (A2) a ligand and (A3) an acid, or
   (B) a catalytic system comprising (B1) a Group VIII metal source of Periodic Table of the Elements except for palladium, (B2) a ligand shown by the following formula (Ib) and (B3) an electron donative compound having an electron donability ΔvD relative to a deuterated methanol D of not less than 2:

wherein A represents a phosphorus atom, an arsenic atom or an antimony atom; and $R^1$, $R^2$ and $R^3$ independently represent a hydrogen atom, an optionally substituted alkyl group, an optionally substituted alkenyl group, an optionally substituted alkynyl group, an optionally substituted cycloalkyl group or an optionally substituted aryl group, or $R^2$ and $R^3$ may together form an optionally substituted alkylene group, with a proviso that $R^1$ to $R^3$ are not concurrently hydrogen atoms.

2. A catalytic system for carbonylation as claimed in claim 1, wherein said Group VIII metal source (A1) in said catalytic system (A) is at least one metal selected from the group consisting of cobalt, nickel, rhodium, palladium and platinum, or a compound of said metal.

3. A catalytic system for carbonylation as claimed in claim 1, wherein said carrier in said catalytic system (A) is at least one member selected from the group consisting of an activated carbon, a metal oxide, a nonmetal oxide and a clay mineral.

4. A catalytic system for carbonylation as claimed in claim 1, wherein said carrier in said catalytic system (A) has a specific surface area of 10 to 3,000 m²/g.

5. A catalytic system for carbonylation as claimed in claim 1, wherein the supporting amount of said Group VIII metal source (A1) in said catalytic system (A) is 0.01 to 20% by weight relative to the carrier.

6. A catalytic system for carbonylation as claimed in claim 1, wherein said ligand (A2) in said catalytic system (A) is at least one member selected from the group consisting of a phosphorus compound, an arsenic compound and an antimony compound.

7. A catalytic system for carbonylation as claimed in claim 1, wherein said ligand (A2) in said catalytic system (A) is a tertiary organic phosphine or a tertiary organic arsine.

8. A catalytic system for carbonylation as claimed in claim 7, wherein said tertiary organic phosphine or tertiary organic arsine has an aryl group, a substituted aryl group or an aromatic heterocyclic group containing a nitrogen atom as a hetero atom.

9. A catalytic system for carbonylation as claimed in claim 1, wherein said Group VIII metal source (B1) in said catalytic system (B) is at least one metal selected from the group consisting of platinum, cobalt, nickel and rhodium, or a compound of said metal.

10. A catalytic system for carbonylation as claimed in claim 1, wherein said catalytic system (B) comprises the ligand (B2) of the formula (Ib) where A is a phosphorus atom.

11. A catalytic system for carbonylation as claimed in claim 1, wherein said ligand (B2) in said catalytic system (B) is a compound of the formula (Ib) where at least one of $R^1$ to $R^3$ is an aryl group or a substituted aryl group.

12. A catalytic system for carbonylation as claimed in claim 1, wherein said ligand (B2) in said catalytic system (B) is a tertiary organic phosphine.

13. A catalytic system for carbonylation as claimed in claim 1, wherein said electron donative compound (B3) in said catalytic system (B) is at least one member selected from the group consisting of an amine, an imine, an amide, an ether, a ketone, an ester, a lactone, an aldehyde, a sulfoxide, a nitrile, a nitro compound, an aromatic hydrocarbon and an aliphatic hydrocarbon.

14. A catalytic system for carbonylation as claimed in claim 1, wherein said electron donative compound (B3) in said catalytic system (B) comprises at least one basic compound selected from the group consisting of an amine, an imine and an amide.

15. A catalytic system for carbonylation as claimed in claim 14, wherein said electron donative compound (B3) in said catalytic system (B) further comprises an ether or an ester.

16. A catalytic system for carbonylation as claimed in claim 1, wherein said electron donative compound (B3) in said catalytic system (B) is a secondary amine or a tertiary amine.

17. A catalytic system for carbonylation as claimed in claim 1, wherein said electron donative compound (B3) in said catalytic system (B) is a compound having an electron donability ΔvD relative to a deuterated methanol D of 30 to 250.

18. A catalytic system for carbonylation as claimed in claim 1, wherein said catalytic system (B) comprises (B1) a platinum compound, (B2) a tertiary organic phosphine having at least one aryl group or substituted aryl group and (B3) an electron donative compound having an electron donability ΔvD relative to a deuterated methanol D of 50 to 250.

19. A catalytic system for carbonylation as claimed in claim 18, wherein said electron donative compound (B3) is a heterocyclic amine or an alkanolamine.

20. A catalytic system for carbonylation as claimed in claim 1, wherein said catalytic system (B) further comprises (B4) an acid.

21. A catalytic system for carbonylation as claimed in claim 1 or 20, wherein said acid (A3) or (B4) is a proton acid or a Lewis acid.

22. A catalytic system for carbonylation as claimed in claim 21, wherein said proton acid is at least one member selected from the group consisting of an arylsulfonic acid, an alkylsulfonic acid, a carboxylic acid, a hydrohalogenic acid, sulfuric acid, nitric acid, a phosphoric acid and a perhalogenic acid.

23. A catalytic system for carbonylation which comprises;
   (A) a combination of (A1) a palladium source, said palladium source being supported on a carrier having a specific surface area of 100 to 2,000 m²/g, (A2) a tertiary organic phosphine or a tertiary organic arsine and (A3) a proton acid, or
   (B) a combination of (B1) a platinum compound, (B2) a tertiary organic phosphine, said organic phosphine having at least one aryl group or substituted aryl group and being free from a nitrogen-containing heterocyclic group, (B3) an electron donative compound having an electron donability ΔvD relative to a deuterated methanol D of not less than 2, and (B4) a proton acid.

24. A catalytic system for carbonylation as claimed in claim 1, wherein the catalytic system is (A) and wherein said Group VIII metal source (A1) in said catalytic system (A) is at least one metal selected from the group consisting of cobalt, nickel, rhodium, palladium and platinum, or a compound of said metal.

25. A catalytic system for carbonylation as claimed in claim 1, wherein the catalytic system is (A) and wherein said ligand (A2) in said catalytic system (A) is at least one member selected from the group consisting of a phosphorus compound, an arsenic compound and an antimony compound.

26. A catalytic system for carbonylation as claimed in claim 1, wherein the catalytic system is (B) and wherein said Group VIII metal source (B1) in said catalytic system (B) is at least one metal selected from the group consisting of platinum, cobalt, nickel and rhodium, or a compound of said metal.

27. A catalytic system for carbonylation as claimed in claim 1, wherein the catalytic system is (B) and wherein said catalytic system (B) comprises the ligand (B2) of the formula (Ib) wherein A is a phosphorus compound.

28. A catalytic system for carbonylation as claimed in claim 1, wherein the catalytic system is (B) and wherein said electron donative compound (B3) in said catalytic system (B) is at least one member selected from the group consisting of an amine, an imine, an amide, an ether, a ketone, an ester, a lactone, an aldehyde, a sulfoxide, a nitrile, a nitro compound, an aromatic hydrocarbon and an aliphatic hydrocarbon.

* * * * *